United States Patent
Merkel et al.

[11] Patent Number: 5,994,038
[45] Date of Patent: Nov. 30, 1999

[54] PHOTOGRAPHIC ELEMENT CONTAINING ACETAMIDO DIR COUPLER

[75] Inventors: Paul B. Merkel, Victor; Jerrold N. Poslusny, Rochester; David A. Steele; Thomas R. Welter, both of Webster, all of N.Y.

[73] Assignee: Eastman Kodak Company, Rochester, N.Y.

[21] Appl. No.: 09/069,263

[22] Filed: Apr. 29, 1998

[51] Int. Cl.$^6$ ............................................. G03C 7/46
[52] U.S. Cl. ........................ 430/389; 430/557; 430/544
[58] Field of Search ................................. 430/388, 389, 430/556, 557, 544

[56] References Cited

U.S. PATENT DOCUMENTS

| | | | |
|---|---|---|---|
| Re. 29,379 | 8/1977 | Shiba et al. | 430/543 |
| 3,933,500 | 1/1976 | Shiba et al. | 430/505 |
| 5,314,797 | 5/1994 | Yoshioka et al. | 430/546 |
| 5,338,651 | 8/1994 | Naruse et al. | 430/557 |
| 5,362,617 | 11/1994 | Morigaki et al. | 430/557 |
| 5,374,507 | 12/1994 | Yoshioka | 430/557 |
| 5,612,174 | 3/1997 | Takizawa et al. | 430/557 |
| 5,674,667 | 10/1997 | Clark et al. | 430/557 |

FOREIGN PATENT DOCUMENTS

| | | |
|---|---|---|
| 2109P98 | 9/1991 | Japan . |
| 4-278942 | 10/1992 | Japan . |
| 5005974 | 5/1993 | Japan . |

*Primary Examiner*—Geraldine Letscher
*Attorney, Agent, or Firm*—Arthur E. Kluegel

[57] ABSTRACT

The invention provides a photographic element, comprising a support bearing at least one silver halide emulsion and at least one 3-indoloylacetanilide yellow dye-forming DIR coupler of structure I, below:

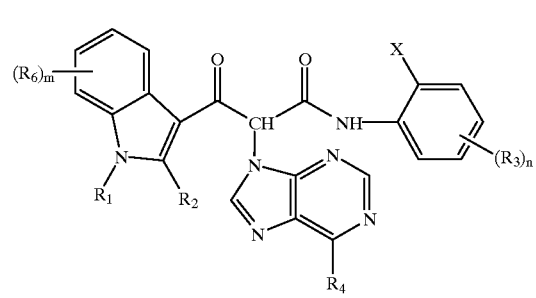

wherein:

$R_1$ is an alkyl or phenyl group;

$R_2$ is a phenyl, t-butyl, cyclohexyl or naphthyl group;

X is a halogen atom or an alkoxy or alkyl group;

each $R_3$ is in the para position or either meta position relative to the anilino nitrogen and is individually selected from the group consisting of halogen atoms, and alkyl, phenyl, alkoxy, phenoxy, carbamoyl, sulfamoyl, carbonamido, sulfonamido, alkylsulfonyl, arylsulfonyl, alkoxycarbonyl, aryloxycarbonyl, acyloxy, sulfoxyl, sulfonyloxy, alkylthio, acyl and cyano groups;

n is 1, 2 or 3;

$R_4$ contains at least two carbon atoms and is an alkylthio group or a carbonamido group represented by —NHCOR$_5$, wherein $R_5$ contains at least four carbon atoms and is an alkyl, phenyl, alkoxy or phenoxy group;

each $R_6$ is individually a halogen atom, an alkyl group or an alkoxy group and m is 0–4;

provided that substituents may join to form a ring.

17 Claims, No Drawings

PHOTOGRAPHIC ELEMENT CONTAINING ACETAMIDO DIR COUPLER

FIELD OF INVENTION

This invention relates to a photographic element comprising a support bearing at least one silver halide emulsion and at least one 3-indoloylacetanilide yellow dye-forming DIR coupler having a purine-type coupling-off group.

BACKGROUND OF INVENTION

In a silver halide color photographic element or material a color image is formed when the element is given an imagewise exposure to light and then subjected to a color development process. In the color development process silver halide is reduced to silver as a function of exposure by a color developing agent, which is oxidized and then reacts with coupler to form dye. In most color photographic elements the coupler or couplers are coated in the element in the form of small dispersion droplets. Many photographic elements or materials contain, in addition to imaging couplers, image-modifying couplers that release a photographically useful group from the coupling site upon reaction with oxidized color developer. Couplers that release a silver development inhibitor from the coupling-off position, so-called DIR couplers, are one type of imaging modifying coupler utilized in color photographic elements.

Many photographic materials, and especially color negative films, contain DIR (development inhibitor releasing) couplers. In addition to forming imaging dye, DIR couplers release inhibitors that can restrain silver development in the layer in which release occurs as well as in other layers of a multilayer photographic material. DIR couplers can help control gamma or contrast, can enhance sharpness or acutance, can reduce granularity and can provide color correction via interlayer interimage effects. There has been a need for more effective yellow dye-forming DIR couplers. Yellow DIR couplers that provide high interimage color correction are particularly desirable for modern color negative films. In addition, it is desirable that such couplers have high activity to maximize rates and efficiencies of inhibitor release and minimize laydowns. DIR couplers that show acceptably low continued coupling when films containing them are placed in a bleach solution immediately after development (i.e. with no intervening stop bath) are also needed. It is also desirable that the inhibitors released from DIR couplers are readily hydrolyzed to weak inhibitors in the developer solution to prevent seasoning of the developer on extended use. It is further desirable that DIR couplers are thermally stable so that materials that incorporate them possess good raw stock stability. In addition, it is desirable that DIR couplers form dyes that have high extinction coefficients and good thermal stability. The DIR couplers of this invention possess all of these desirable properties, especially high activity, the propensity to provide good interlayer interimage, the release of efficient hydrolyzable inhibitors, high dye extinction coefficients and excellent dye stability.

U.S. Pat. No. 3,933,500 broadly discloses DIR couplers with azole coupling-off groups, but discloses neither the 3-indoloylacetanilide coupler parents nor the purine coupling-off groups of this invention. U.S. patent application Ser. No. 08/824,223 discloses yellow dye-forming couplers with purine coupling-off groups, but does not disclose the 3-indoloylacetanilide DIR couplers of this invention. U.S. Pat. No. 5,674,667 (EPA 751,428 A1) discloses pyrroloylacetanilide yellow dye-forming couplers with a variety of coupling-off groups. The pyrroloylacetanilide couplers of U.S. Pat. No. 5,674,667 are structurally distinct from the 3-indoloylacetanilde couplers of this invention and lack the major advantages of the couplers of this invention.

SUMMARY OF THE INVENTION

The invention provides a photographic element, comprising a support bearing at least one silver halide emulsion and at least one 3-indoloylacetanilide yellow dye-forming DIR coupler of structure I, below:

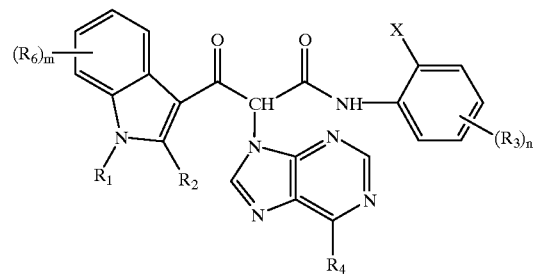

wherein:

$R_1$ is an alkyl or phenyl group;

$R_2$ is a phenyl, t-butyl, cyclohexyl or naphthyl group;

X is a halogen atom or an alkoxy or alkyl group;

each $R_3$ is in the para position or either meta position relative to the anilino nitrogen and is individually selected from the group consisting of halogen atoms, and alkyl, phenyl, alkoxy, phenoxy, carbamoyl, sulfamoyl, carbonamido, sulfonamido, alkylsulfonyl, arylsulfonyl, alkoxycarbonyl, aryloxycarbonyl, acyloxy, sulfoxyl, sulfonyloxy, alkylthio, acyl and cyano groups;

n is 1, 2 or 3;

$R_4$ contains at least two carbon atoms and is an alkylthio group or a carbonamido group represented by —NHCOR$_5$, wherein $R_5$ contains at least four carbon atoms and is an alkyl, phenyl, alkoxy or phenoxy group;

each $R_6$ is individually a halogen atom, an alkyl group or an alkoxy group and m is 0–4;

provided that substituents may join to form a ring.

The invention also provides a method for forming an image and a coupler compound.

Elements of the invention exhibit improved development inhibiting ability.

DETAILED DESCRIPTION OF THE INVENTION

This invention relates to a photographic element comprising a support bearing at least one silver halide emulsion and at least one 3-indoloylacetanilide yellow dye-forming DIR coupler of structure I, below:

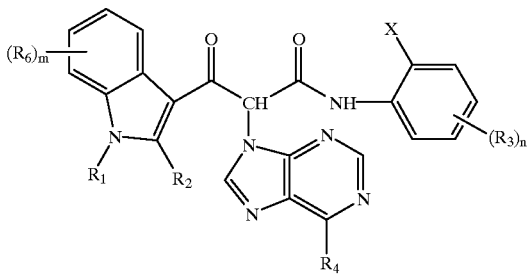

I wherein:

$R_1$ is an alkyl or phenyl group;

$R_2$ is a phenyl, t-butyl, cyclohexyl or naphthyl group;

X is a halogen atom or an alkoxy or alkyl group;

each $R_3$ is in the para position or either meta position relative to the anilino nitrogen and is individually selected from the group consisting of halogen atoms, and alkyl, phenyl, alkoxy, phenoxy, carbamoyl, sulfamoyl, carbonamido, sulfonamido, alkylsulfonyl, arylsulfonyl, alkoxycarbonyl, aryloxycarbonyl, acyloxy, sulfoxyl, sulfonyloxy, alkylthio, acyl and cyano groups;

n is 1, 2 or 3;

$R_4$ contains at least two carbon atoms and is an alkylthio group or a carbonamido group represented by —$NHCOR_5$, wherein $R_5$ contains at least four carbon atoms and is an alkyl, phenyl, alkoxy or phenoxy group;

each $R_6$ is individually a halogen atom, an alkyl group or an alkoxy group and m is 0–4;

provided that substituents may join to form a ring.

In a useful embodiment $R_1$ is an alkyl group. In a preferred embodiment $R_2$ is a phenyl group. In another useful embodiment X is a halogen atom, such as chlorine or fluorine. In further useful embodiments n is 1 and $R_3$ is a carbamoyl group or a sulfamoyl group in either the 4- or 5- position relative to the NH group (X being in the 2- position). In another useful embodiment, m is 0.

In a preferred embodiment $R_4$ is an alkylthio group of the form —$SCH_2CO_2R_7$, wherein $R_7$ is an alkyl group with at least two carbon atoms or a phenyl group. In a particularly preferred embodiment, $R_7$ is an alkyl group with three to seven carbon atoms. When $R_4$ is a carbonamido group, $R_5$ preferably contains five to eleven carbon atoms.

Preferably, one or more 3-indoloylacetanilide DIR couplers of this invention is coated in the same layer with one or more blue-sensitive silver halide emulsions in the photographic elements of this invention. Blue-sensitive tabular grain emulsions, as described below, are particularly useful in the photographic elements of this invention.

The alkyl groups comprising $R_1$–$R_3$, $R_5$–$R_7$ and X may be straight chain, branched or cyclic and may be unsubstituted or substituted. The alkoxy groups comprising $R_3$, $R_5$, $R_6$ and X may be unbranched or branched and may be unsubstituted or substituted. The phenyl groups comprising $R_1$, $R_2$, $R_5$ and $R_7$ and the phenoxy groups comprising $R_3$ and $R_5$ may also be substituted or unsubstituted. The carbonamido and alkylthio groups comprising $R_3$ and $R_4$ may be unsubstituted or substituted. The carbamoyl, sulfamoyl, sulfonamido, alkylsulfonyl, arylsulfonyl, alkoxycarbonyl, aryloxycarbonyl, acyloxy, sulfoxyl, sulfonyloxy and acyl groups comprising $R_3$ may also be substituted. Any substituent may be chosen to further substitute the $R_1$–$R_7$ and X groups of this invention that does not adversely affect the performance of the 3-indoloylacetanilide couplers of this invention. Suitable substituents include halogen atoms, such as chlorine, alkenyl groups, alkynyl groups, aryl groups, hydroxy groups, alkoxy groups, aryloxy groups, acyl groups, acyloxy groups, alkoxycarbonyl groups, aryloxycarbonyl groups, carbonamido groups (including alkyl-, aryl-, alkoxy-, aryloxy- and alkylamino- carbonamido groups), carbamoyl groups, carbamoyloxy groups, sulfonamido groups, sulfamoyl groups, alkylthio groups, arylthio groups, sulfoxyl groups, sulfonyl groups, sulfonyloxy groups, alkoxysulfonyl groups, aryloxysulfonyl groups, trifluoromethyl groups, cyano groups, imido groups and heterocyclic groups, such as 2-furyl, 3-furyl, 2-thienyl, 1-pyrrolyl, 2-pyrrolyl, 1-imidazolyl and N-succinimidyl groups. The phenyl groups comprising $R_1$, $R_2$, $R_5$ and $R_7$ and the phenoxy groups comprising $R_3$ and $R_5$ may also be substituted with one or more unbranched, branched or cyclic alkyl groups.

Useful coated levels of 3-indoloylacetanilide DIR couplers of this invention range from about 0.005 to about 0.60 g/sq m, or more typically from 0.010 to 0.30 g/sq m.

The 3-indoloylacetanalide couplers of this invention may be utilized by dissolving them in high-boiling coupler solvents and then dispersing the organic coupler plus coupler solvent mixtures as small particles in aqueous solutions of gelatin and surfactant (via milling or homogenization). Removable auxiliary organic solvents such as ethyl acetate or cyclohexanone may also be used in the preparation of such dispersions to facilitate the dissolution of the coupler in the organic phase. Coupler solvents useful for the practice of this invention include aryl phosphates (e.g. tritolyl phosphate), alkyl phosphates (e.g. trioctyl phosphate), mixed aryl alkyl phosphates (e.g. diphenyl 2-ethylhexyl phosphate), aryl, alkyl or mixed aryl alkyl phosphonates, phosphine oxides (e.g. trioctylphosphine oxide), esters of aromatic acids (e.g. dibutyl phthalate, octyl benzoate, or benzyl salicylate) esters of aliphatic acids (e.g. acetyl tributyl citrate or dibutyl sebecate), alcohols (e.g. oleyl alcohol), phenols (e.g. p-dodecylphenol), carbonamides (e.g. N,N-dibutyldodecanamide or N-butylacetanalide), sulfoxides (e.g. bis(2-ethylhexyl)sulfoxide), sulfonamides (e.g. N,N-dibutyl-p-toluenesulfonamide) or hydrocarbons (e.g. dodecylbenzene). Additional coupler solvents and auxiliary solvents are noted in Research Disclosure, December 1989, Item 308119, p 993. Useful coupler:coupler solvent weight ratios range from about 1:0.1 to 1:8.0, with 1:0.3 to 1:2.0 being preferred. The 3-indoloylacetanilide couplers of this invention may also be dispersed and coated in latex particles or may be dispersed and coated without a high-boiling solvent or latex.

Besides exhibiting improved development inhibiting ability, embodiments of the invention yield dyes with improved extinction coefficients and improved thermal or dark stability. The high activity, efficient inhibition and high dye extinction coefficients associated with the DIR couplers of this invention can permit reductions in laydowns, which can provide layer thinning and improved sharpness. Coupler embodiments also have excellent thermal stability, which provides photographic elements with improved raw stock stability. Superior thermal stability of the yellow dyes formed from the DIR couplers of this invention enhances the image permanence of processed photographic elements of this invention upon long term storage or storage at elevated temperatures.

A further advantage of embodiments of this invention is that the absorption spectra of the yellow dyes formed form the 3-indoloylacetanilide DIR couplers of this invention are sharper cutting on the long wavelength side and produce less unwanted green light absorption and truer and more saturated yellow colors. Embodiments also provide the advantages of low density variability in response to variations in developer pH and low continued coupling when the elements are processed in a bleach solution directly after removal from developer solution. DIR couplers of this invention can also release inhibitors that readily hydrolyze in developer solutions to form either noninhibitors or very weak inhibitors. This can reduce or eliminate the undesirable sensitometric effects that can occur, if a strong inhibitor diffuses out of a photographic material and accumulates in a color developer solution.

Examples of purine-releasing 3-indoloylacetanilide DIR couplers of this invention include, but are not limited to, A1–A18, below:

A1
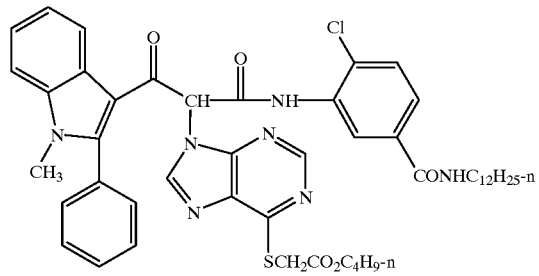

A2
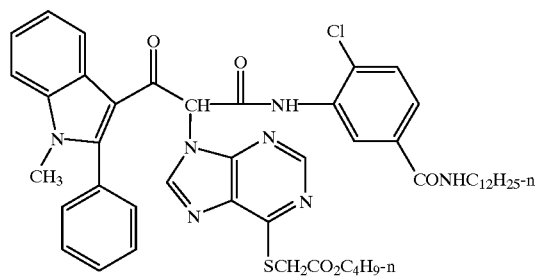

A3
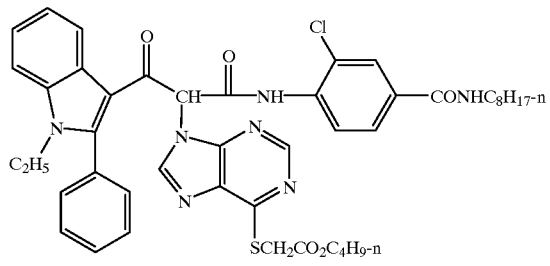

A4
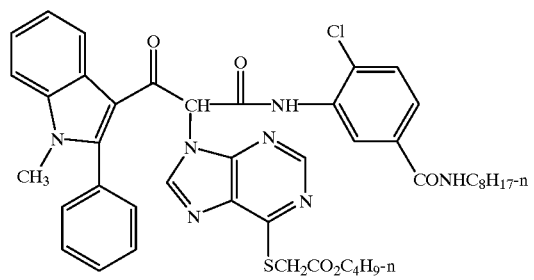

-continued

A5
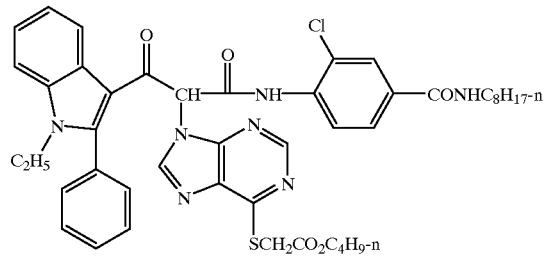

A6
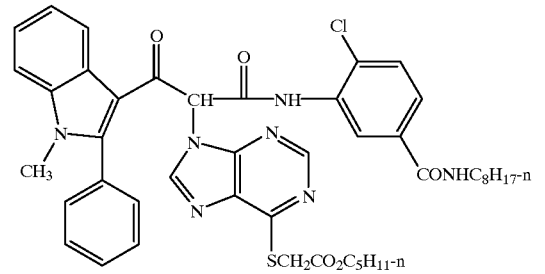

A7
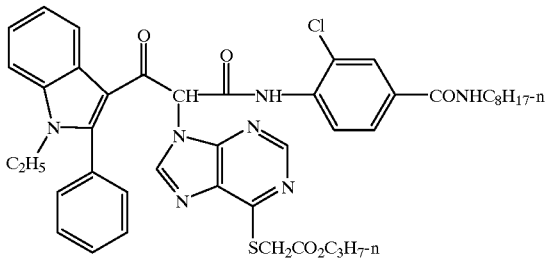

A8
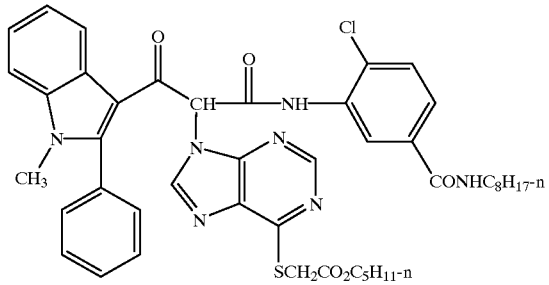

A9
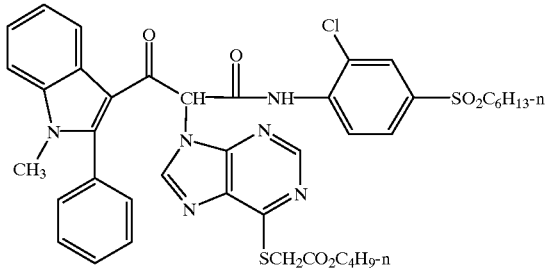

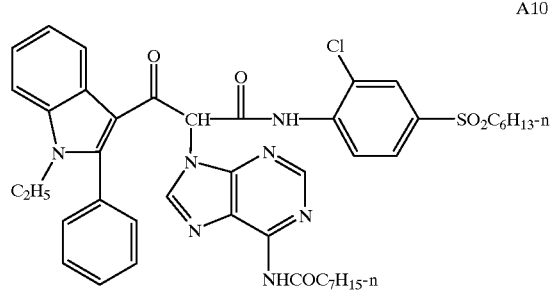

A10

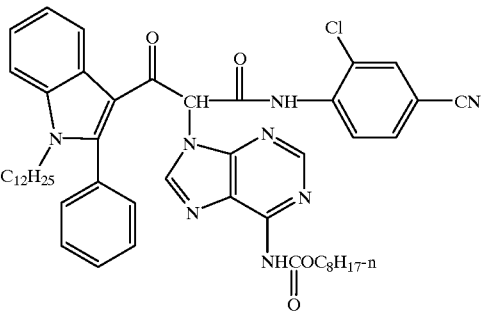

A15

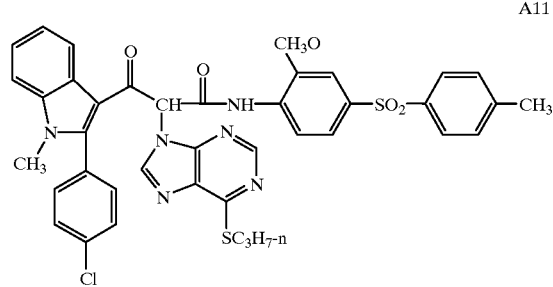

A11

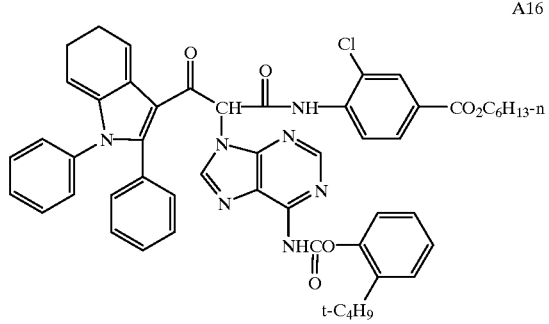

A16

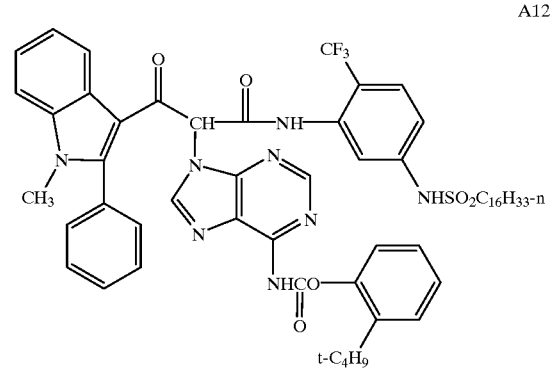

A12

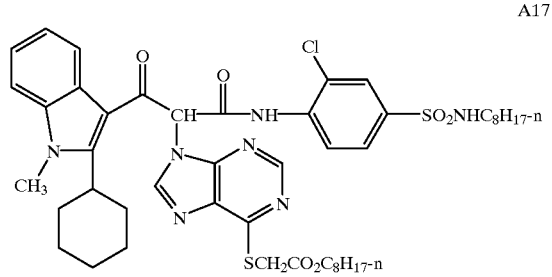

A17

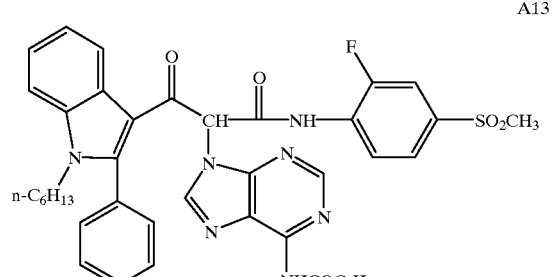

A13

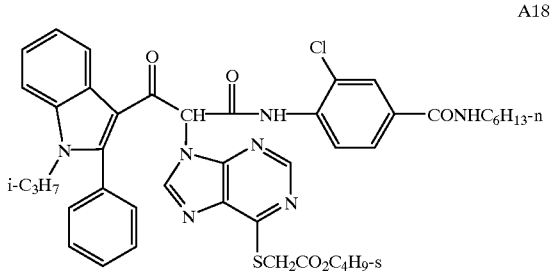

A18

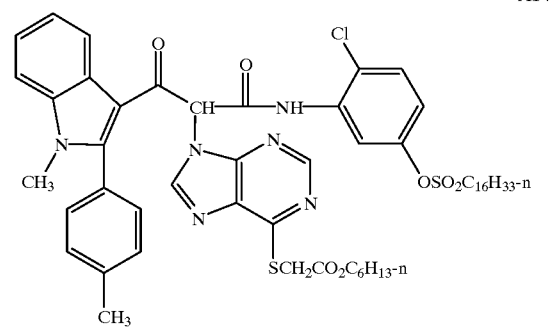

A14

The couplers of this invention may be used together with a variety of other types of couplers in the same layer or in different layers of a multilayer photographic material. Specifically contemplated is the use of the 3-indoloylacetanilide DIR couplers of this invention in blue-sensitive photographic elements together with one or more yellow dye-forming imaging couplers, such couplers Y-1 and Y-2, below:

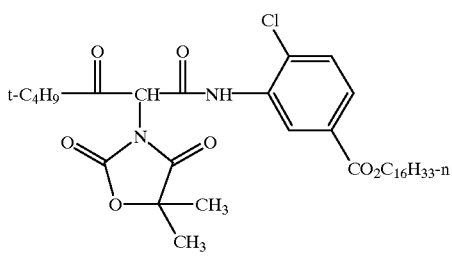

Y-1

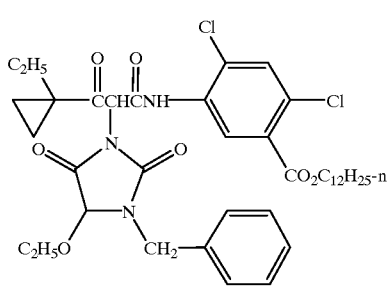

Y-2

Unless otherwise specifically stated, the term substituted or substituent means any group or atom other than hydrogen bonded to the remainder of a molecule. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin- 1 -yl, 2-oxo-5-tetradecylpyrrolin- 1 -yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a silver halide emulsion and the emulsion coated as a layer on a support to form part of a photographic element. Alternatively, unless provided otherwise, they can be incorporated at a location adjacent to the silver halide emulsion layer where, during development, they will be in reactive association with development products such as oxidized color developing agent. Thus, as used herein, the term "associated" signifies that the compound is in the silver halide emulsion layer or in an adjacent location where, during processing, it is capable of reacting with silver halide development products.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The photographic elements can be single color elements or multicolor elements. Multicolor elements contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

If desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND, and as described in Hatsumi Kyoukai Koukai Gihou No. 94-6023, published Mar. 15, 1994, available from the Japanese Patent Office, the contents of which are incorporated herein by reference. When it is desired to employ the inventive materials in a small format film, *Research Disclosure*, June 1994, Item 36230, provides suitable embodiments.

In the following discussion of suitable materials for use in the emulsions and elements of this invention, reference will be made to *Research Disclosure*, September 1996, Item 38957, available as described above, which is referred to herein by the term "Research Disclosure". The contents of the Research Disclosure, including the patents and publications referenced therein, are incorporated herein by reference, and the Sections hereafter referred to are Sections of the Research Disclosure.

Except as provided, the silver halide emulsion containing elements employed in this invention can be either negative-working or positive-working as indicated by the type of processing instructions (i.e. color negative, reversal, or direct positive processing) provided with the element. Suitable emulsions and their preparation as well as methods of chemical and spectral sensitization are described in Sections I through V. Various additives such as UV dyes, brighteners, antifoggants, stabilizers, light absorbing and scattering materials, and physical property modifying addenda such as hardeners, coating aids, plasticizers, lubricants and matting agents are described, for example, in Sections II and VI through VIII. Color materials are described in Sections X through XIII. Suitable methods for incorporating couplers and dyes, including dispersions in organic solvents, are described in Section X(E). Scan facilitating is described in Section XIV. Supports, exposure, development systems, and processing methods and agents are described in Sections XV to XX. The information contained in the September 1994 *Research Disclosure*, Item No. 36544 referenced above, is updated in the September 1996 *Research Disclosure*, Item No. 38957. Certain desirable photographic elements and processing steps, including those useful in conjunction with color reflective prints, are described in *Research Disclosure*, Item 37038, February 1995.

Coupling-off groups are well known in the art. Such groups can determine the chemical equivalency of a coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as dye formation, dye hue adjustment, development acceleration or inhibition, bleach acceleration or inhibition, electron transfer facilitation, color correction and the like.

The presence of hydrogen at the coupling site provides a 4-equivalent coupler, and the presence of another coupling-off group usually provides a 2-equivalent coupler. Representative classes of such coupling-off groups include, for example, chloro, alkoxy, aryloxy, hetero-oxy, sulfonyloxy, acyloxy, acyl, heterocyclyl, sulfonamido, mercaptotetrazole, benzothiazole, mercaptopropionic acid, phosphonyloxy, arylthio, and arylazo. These coupling-off groups are described in the art, for example, in U.S. Pat. Nos. 2,455, 169, 3,227,551, 3,432,521, 3,476,563, 3,617,291, 3,880,661, 4,052,212 and 4,134,766; and in UK. Patents and published application Nos. 1,466,728, 1,531,927, 1,533,039, 2,006, 755A and 2,017,704A, the disclosures of which are incorporated herein by reference.

Image dye-forming couplers may be included in the element such as couplers that form cyan dyes upon reaction with oxidized color developing agents which are described in such representative patents and publications as: "Farbkuppler-eine Literature Ubersicht," published in Agfa Mitteilungen, Band III, pp. 156–175 (1961) as well as in U.S. Pat. Nos. 2,367,531; 2,423,730; 2,474,293; 2,772,162; 2,895,826; 3,002,836; 3,034,892; 3,041,236; 4,333,999; 4,746,602; 4,753,871; 4,770,988; 4,775,616; 4,818,667; 4,818,672; 4,822,729; 4,839,267; 4,840,883; 4,849,328; 4,865,961; 4,873,183; 4,883,746; 4,900,656; 4,904,575; 4,916,051; 4,921,783; 4,923,791; 4,950,585; 4,971,898; 4,990,436; 4,996,139; 5,008,180; 5,015,565; 5,011,765; 5,011,766; 5,017,467; 5,045,442; 5,051,347; 5,061,613; 5,071,737; 5,075,207; 5,091,297; 5,094,938; 5,104,783; 5,178,993; 5,813,729; 5,187,057; 5,192,651; 5,200,305 5,202,224; 5,206,130; 5,208,141; 5,210,011; 5,215,871; 5,223,386; 5,227,287; 5,256,526; 5,258,270; 5,272,051; 5,306,610; 5,326,682; 5,366,856; 5,378,596; 5,380,638; 5,382,502; 5,384,236; 5,397,691; 5,415,990; 5,434,034; 5,441,863; EPO 0 246 616; EPO 0 250 201; EPO 0 271 323;

EPO 0 295 632; EPO 0 307 927; EPO 0 333 185; EPO 0 378 898; EPO 0 389 817; EPO 0 487 111; EPO 0 488 248; EPO 0 539 034; EPO 0 545 300; EPO 0 556 700; EPO 0 556 777; EPO 0 556 858; EPO 0 569 979; EPO 0 608 133; EPO 0 636 936; EPO 0 651 286; EPO 0 690 344; German OLS 4,026,903; German OLS 3,624,777. and German OLS 3,823,049. Typically such couplers are phenols, naphthols, or pyrazoloazoles.

Couplers that form magenta dyes upon reaction with oxidized color developing agent are described in such representative patents and publications as: "Farbkuppler-eine Literature Ubersicht," published in Agfa Mitteilungen, Band III, pp. 126–156 (1961) as well as U.S. Pat. Nos. 2,311,082 and 2,369,489; 2,343,701; 2,600,788; 2,908,573; 3,062,653; 3,152,896; 3,519,429; 3,758,309; 3,935,015; 4,540,654; 4,745,052; 4,762,775; 4,791,052; 4,812,576; 4,835,094; 4,840,877; 4,845,022; 4,853,319; 4,868,099; 4,865,960; 4,871,652; 4,876,182; 4,892,805; 4,900,657; 4,910,124; 4,914,013; 4,921,968; 4,929,540; 4,933,465; 4,942,116; 4,942,117; 4,942,118; U.S. Pat. Nos. 4,959,480; 4,968,594; 4,988,614; 4,992,361; 5,002,864; 5,021,325; 5,066,575; 5,068,171; 5,071,739; 5,100,772; 5,110,942; 5,116,990; 5,118,812; 5,134,059; 5,155,016; 5,183,728; 5,234,805; 5,235,058; 5,250,400; 5,254,446; 5,262,292; 5,300,407; 5,302,496; 5,336,593; 5,350,667; 5,395,968; 5,354,826; 5,358,829; 5,368,998; 5,378,587; 5,409,808; 5,411,841; 5,418,123; 5,424,179; EPO 0 257 854; EPO 0 284 240; EPO 0 341 204; EPO 347,235; EPO 365,252; EPO 0 422 595; EPO 0 428 899; EPO 0 428 902; EPO 0 459 331; EPO 0 467 327; EPO 0 476 949; EPO 0 487 081; EPO 0 489 333; EPO 0 512 304; EPO 0 515 128; EPO 0 534 703; EPO 0 554 778; EPO 0 558 145; EPO 0 571 959; EPO 0 583 832; EPO 0 583 834; EPO 0 584 793; EPO 0 602 748; EPO 0 602 749; EPO 0 605 918; EPO 0 622 672; EPO 0 622 673; EPO 0 629 912; EPO 0 646 841, EPO 0 656 561; EPO 0 660 177; EPO 0 686 872; WO 90/10253; WO 92/09010; WO 92/10788; WO 92/12464; WO 93/01523; WO 93/02392; WO 93/02393; WO 93/07534; UK Application 2,244,053; Japanese Application 03192-350; German OLS 3,624,103; German OLS 3,912,265; and German OLS 40 08 067. Typically such couplers are pyrazolones, pyrazoloazoles, or pyrazolobenzimidazoles that form magenta dyes upon reaction with oxidized color developing agents.

Couplers that form yellow dyes upon reaction with oxidized color developing agent are described in such representative patents and publications as: "Farbkuppler-eine Literature Ubersicht," published in Agfa Mitteilungen; Band III; pp. 112–126 (1961); as well as U.S. Pat. Nos. 2,298,443; 2,407,210; 2,875,057; 3,048,194; 3,265,506; 3,447,928; 4,022,620; 4,443,536; 4,758,501; 4,791,050; 4,824,771; 4,824,773; 4,855,222; 4,978,605; 4,992,360; 4,994,361; 5,021,333; 5,053,325; 5,066,574; 5,066,576; 5,100,773; 5,118,599; 5,143,823; 5,187,055; 5,190,848; 5,213,958; 5,215,877; 5,215,878; 5,217,857; 5,219,716; 5,238,803; 5,283,166; 5,294,531; 5,306,609; 5,328,818; 5,336,591; 5,338,654; 5,358,835; 5,358,838; 5,360,713; 5,362,617; 5,382,506; 5,389,504; 5,399,474; 5,405,737; 5,411,848; 5,427,898; EPO 0 327 976; EPO 0 296 793; EPO 0 365 282; EPO 0 379 309; EPO 0 415 375; EPO 0 437 818; EPO 0 447 969; EPO 0 542 463; EPO 0 568 037; EPO 0 568 196; EPO 0 568 777; EPO 0 570 006; EPO 0 573 761; EPO 0 608 956; EPO 0 608 957; and EPO 0 628 865. Such couplers are typically open chain ketomethylene compounds.

Couplers that form colorless products upon reaction with oxidized color developing agent are described in such representative patents as: UK. 861,138; U.S. Pat. Nos. 3,632, 345; 3,928,041; 3,958,993 and 3,961,959. Typically such couplers are cyclic carbonyl containing compounds that form colorless products on reaction with an oxidized color developing agent.

Couplers that form black dyes upon reaction with oxidized color developing agent are described in such representative patents as U.S. Pat. Nos. 1,939,231; 2,181,944; 2,333,106; and 4,126,461; German OLS No. 2,644,194 and German OLS No. 2,650,764. Typically, such couplers are resorcinols or m-aminophenols that form black or neutral products on reaction with oxidized color developing agent.

In addition to the foregoing, so-called "universal" or "washout" couplers may be employed. These couplers do not contribute to image dye-formation. Thus, for example, a naphthol having an unsubstituted carbamoyl or one substituted with a low molecular weight substituent at the 2- or 3- position may be employed. Couplers of this type are described, for example, in U.S. Pat. Nos. 5,026,628, 5,151, 343, and 5,234,800.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may contain solubilizing groups such as described in U.S. Pat. No. 4,482,629. The coupler may also be used in association with "wrong" colored couplers (e.g. to adjust levels of interlayer correction) and, in color negative applications, with masking couplers such as those described in EP 213, 490; Japanese Published Application 58-172,647; U.S. Pat. Nos. 2,983,608; 4,070,191; and 4,273,861; German Applications DE 2,706,117 and DE 2,643,965; UK. Pat. No. 1,530,272; and Japanese Application 58-113935. The masking couplers may be shifted or blocked, if desired.

Typically, couplers are incorporated in a silver halide emulsion layer in a mole ratio to silver of 0.1 to 1.0 and generally 0.1 to 0.5. Usually the couplers are dispersed in a high-boiling organic solvent in a weight ratio of solvent to coupler of 0.1 to 10.0 and typically 0.1 to 2.0 although dispersions without high-boilling solvent are sometimes employed.

The invention materials may be used in association with materials that release Photographically Useful Groups (PUGS) that accelerate or otherwise modify the processing steps e.g. of bleaching or fixing to improve the quality of the image. Bleach accelerator releasing couplers such as those described in EP 193,389; EP 301,477; U.S. Pat. No. 4,163, 669; U.S. Pat. No. 4,865,956; and U.S. Pat. No. 4,923,784, may be useful. Also contemplated is use of the compositions in association with nucleating agents, development accelerators or their precursors (UK Patent 2,097,140; UK. Patent 2,131,188); electron transfer agents (U.S. Pat. No. 4,859, 578; U.S. Pat. No. 4,912,025); antifogging and anti colormixing agents such as derivatives of hydroquinones, aminophenols, amines, gallic acid; catechol; ascorbic acid; hydrazides; sulfonamidophenols; and non color-forming couplers.

The invention materials may also be used in combination with filter dye layers comprising colloidal silver sol or yellow, cyan, and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543, 323.) Also, the compositions may be blocked or coated in protected form as described, for example, in Japanese Application 61/258,249 or U.S. Pat. No. 5,019,492.

The invention materials may further be used in combination with image-modifying compounds that release PUGS such as "Developer Inhibitor-Releasing" compounds (DIR's). DIR's useful in conjunction with the compositions of the invention are known in the art and examples are described in U.S. Pat. Nos. 3,137,578; 3,148,022; 3,148,062; 3,227,554; 3,384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437; 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365, 346; 373,382; 376,212; 377,463; 378,236; 384,670; 396, 486; 401,612; 401,613.

Such compounds are also disclosed in "Developer-Inhibitor-Releasing (DIR) Couplers for Color Photography," C.R. Barr, J. R. Thirtle and P. W. Vittum in Photographic Science and Engineering, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

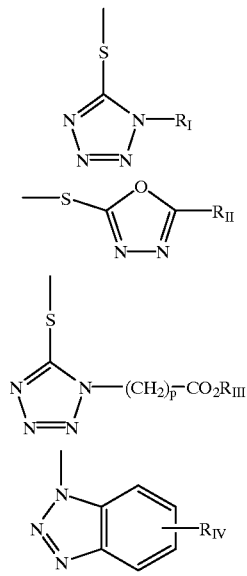

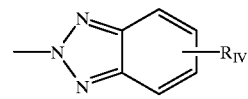

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and —$SR_I$; $R_{III}$ is a straight or branched alkyl group of from 1 to about 5 carbon atoms and p is from 1 to 3; and $R_{IV}$ is selected from the group consisting of hydrogen, halogens and alkoxy, phenyl and carbonamido groups, —$COOR_V$ and —$NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

A compound such as a coupler may release a PUG directly upon reaction of the compound during processing, or indirectly through a timing or linking group. A timing group produces the time-delayed release of the PUG such groups using an intramolecular nucleophilic substitution reaction (U.S. Pat. No. 4,248,962); groups utilizing an electron transfer reaction along a conjugated system (U.S. Pat. Nos. 4,409,323; 4,421,845; 4,861,701, Japanese Applications 57-188035; 58-98728; 58-209736; 58-209738); groups that function as a coupler or reducing agent after the coupler reaction (U.S. Pat. No. 4,438,193; U.S. Pat. No. 4,618,571) and groups that combine the features describe above. It is typical that the timing group is of one of the formulas:

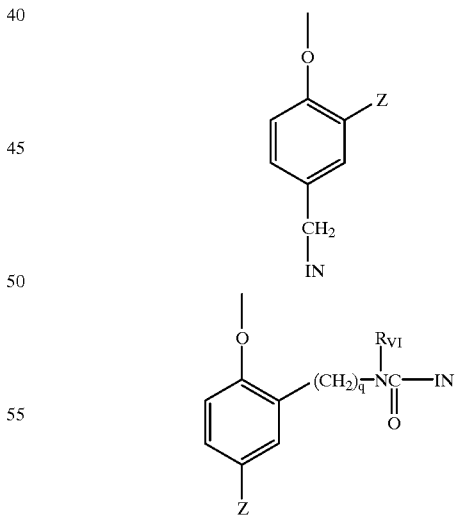

wherein IN is the inhibitor moiety, Z is selected from the group consisting of nitro, cyano, alkylsulfonyl; sulfamoyl (—$SO_2NR_2$); and sulfonamido (—$NRSO_2R$) groups; q is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

The timing or linking groups may also function by electron transfer down an unconjugated chain. Linking groups are known in the art under various names. Often they have been referred to as groups capable of utilizing a hemiacetal or iminoketal cleavage reaction or as groups capable of utilizing a cleavage reaction due to ester hydrolysis such as U.S. Pat. No. 4,546,073. This electron transfer down an unconjugated chain typically results in a relatively fast decomposition and the production of carbon dioxide, formaldehyde, or other low molecular weight by-products. The groups are exemplified in EP 464,612, EP 523,451, U.S. Pat. No. 4,146,396, Japanese Kokai 60-249148 and 60-249149.

Suitable developer inhibitor-releasing couplers for use in the present invention include, but are not limited to, the following:

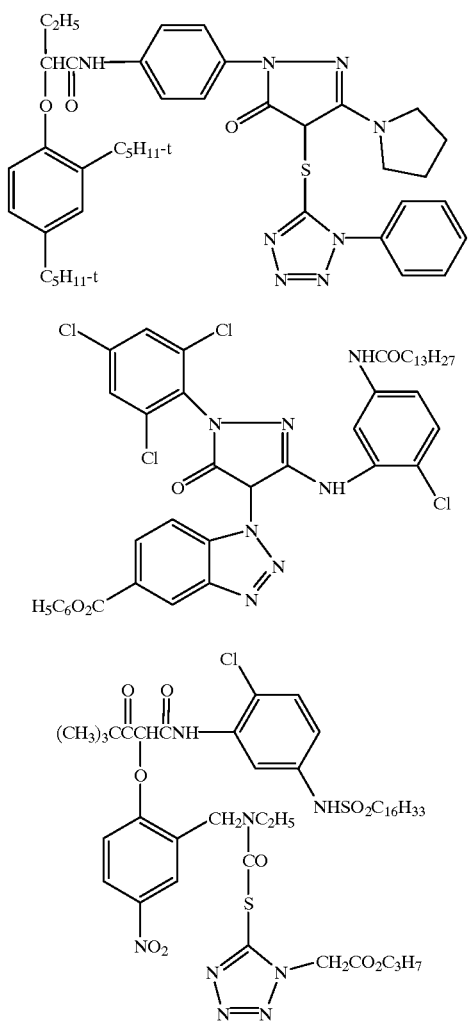

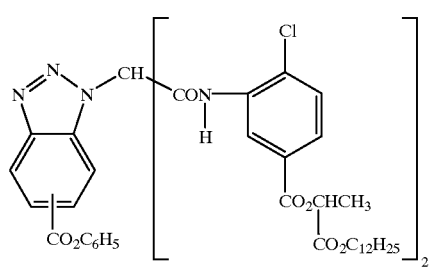

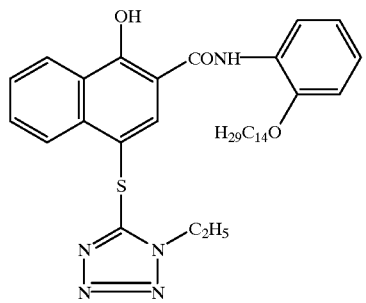

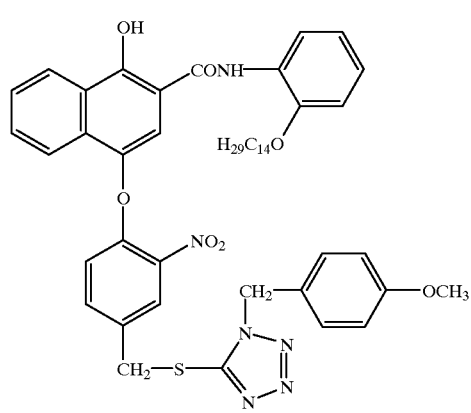

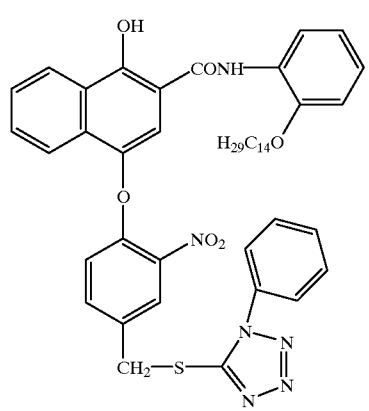

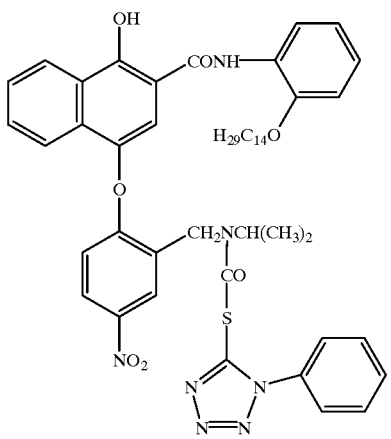
D8

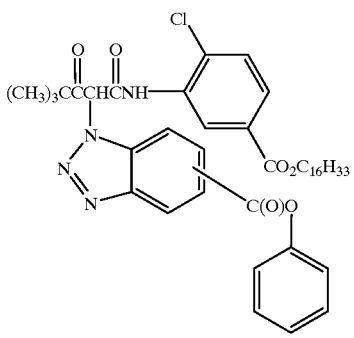
D11

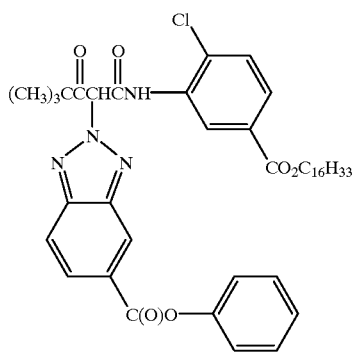
D12

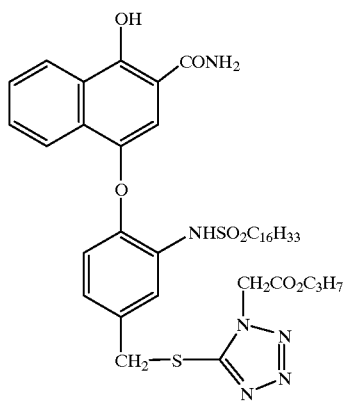
D9

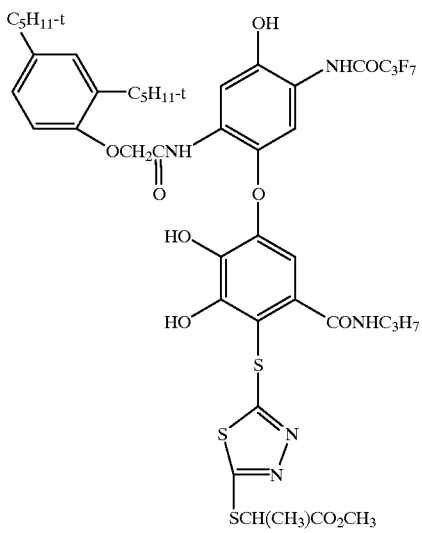
D10

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; on a support with reduced oxygen permeability (EP 553,339); with epoxy solvents (EP 164,961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171. Other compounds useful in combination with the invention are disclosed in Japanese Published Applications described in Derwent Abstracts having accession numbers as follows: 90-072,629, 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Conventional radiation-sensitive silver halide emulsions can be employed in the practice of this invention. Such emulsions are illustrated by *Research Disclosure*, Item 38755, September 1996, I. Emulsion grains and their preparation.

Especially useful in this invention are tabular grain silver halide emulsions. Tabular grains are those having two parallel major crystal faces and having an aspect ratio of at least 2. The term "aspect ratio" is the ratio of the equivalent circular diameter (ECD) of a grain major face divided bt its thickness (t). Tabular grain emulsions are those in which the tabular grains account for at least 50 percent (preferably at least 70 percent and optimally at least 90 percent) of total grain projected area. Preferred tabular grain emulsions are those in which the average thickness of the tabular grains is less than 0.3 micrometer (preferably thin—that is, less than 0.2 micrometer and most preferably ultrathin—that is, less than 0.07 micrometer). The major faces of the tabular grains can lie in either {111 } or {100} crystal planes. The mean ECD of tabular grain emulsions rarely exceeds 10 micrometers and more typically is less than 5 micrometers.

In their most widely used form tabular grain emulsions are high bromide {111 } tabular grain emulsions. Such emulsions are illustrated by Kofron et al U.S. Pat. No. 4,439,520, Wilgus et al U.S. Pat. No. 4,434,226, Solberg et al U.S. Pat. No. 4,433,048, Maskasky U.S. Pat. Nos. 4,435, 501, 4,463,087 and 4,173,320, Daubendiek et al U.S. Pat. Nos. 4,414,310 and 4,914,014, Sowinski et al U.S. Pat. No. 4,656,122, Piggin et al U.S. Pat. Nos. 5,061,616 and 5,061, 609, Tsaur et al U.S. Pat. Nos. 5,147,771, '772, '773, 5,171,659 and 5,252,453, Black et al 5,219,720 and 5,334, 495, Delton U.S. Pat. Nos. 5,310,644, 5,372,927 and 5,460, 934, Wen U.S. Pat. No. 5,470,698, Fenton et al U.S. Pat. No. 5,476,760, Eshelman et al U.S. Pat. Nos. 5,612, 175 and 5,614,359, and Irving et al U.S. Pat. No. 5,667,954.

Ultrathin high bromide {111 } tabular grain emulsions are illustrated by Daubendiek et al U.S. Pat. Nos. 4,672,027, 4,693,964, 5,494,789, 5,503,971 and 5,576,168, Antoniades et al U.S. Pat. No. 5,250,403, Olm et al U.S. Pat. No. 5,503,970, Deaton et al U.S. Pat. No. 5,582,965, and Maskasky U.S. Pat. No. 5,667,955.

High bromide {100} tabular grain emulsions are illustrated by Mignot U.S. Pat. Nos. 4,386,156 and 5,386,156.

High chloride {111 } tabular grain emulsions are illustrated by Wey U.S. Pat. No. 4,399,215, Wey et al U.S. Pat. No. 4,414,306, Maskasky U.S. Pat. Nos. 4,400,463, 4,713, 323, 5,061,617, 5,178,997, 5,183,732, 5,185,239, 5,399,478 and 5,411,852, and Maskasky et al U.S. Pat. Nos. 5,176,992 and 5,178,998. Ultrathin high chloride {111 } tabular grain emulsions are illustrated by Maskasky U.S. Pat. Nos. 5,271, 858 and 5,389,509.

High chloride {100} tabular grain emulsions are illustrated by Maskasky U.S. Pat. Nos. 5,264,337, 5,292,632, 5,275,930 and 5,399,477, House et al U.S. Pat. No. 5,320, 938, Brust et al U.S. Pat. No. 5,314,798, Szajewski et al U.S. Pat. No. 5,356,764, Chang et al U.S. Pat. Nos. 5,413,904 and 5,663,041, Oyamada U.S. Pat. No. 5,593,821, Yamashita et al U.S. Pat. Nos. 5,641,620 and 5,652,088, Saitou et al U.S. Pat. No. 5,652,089, and Oyamada et al U.S. Pat. No. 5,665,530. Ultrathin high chloride {100} tabular grain emulsions can be prepared by nucleation in the presence of iodide, following the teaching of House et al and Chang et al, cited above.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent. Tabular grain emulsions of the latter type are illustrated by Evans et al. U.S. Pat. No. 4,504,570.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye. If desired "Redox Amplification" as described in Research Disclosure XVIIIB(5) may be used.

With negative-working silver halide, the processing step described above provides a negative image. One type of such element, referred to as a color negative film, is designed for image capture. Speed (the sensitivity of the element to low light conditions) is usually critical to obtaining sufficient image in such elements. Such elements are typically silver bromoiodide emulsions coated on a transparent support and may be processed, for example, in known color negative processes such as the Kodak C-41 process as described in The British Journal of Photography Annual of 1988, pages 191–198. If a color negative film element is to be subsequently employed to generate a viewable projection print as for a motion picture, a process such as the Kodak ECN-2 process described in the H-24 Manual available from Eastman Kodak Co. may be employed to provide the color negative image on a transparent support. Color negative development times are typically 3'15" or less and desirably 90 or even 60 seconds or less.

The photographic element of the invention can be incorporated into exposure structures intended for repeated use or exposure structures intended for limited use, variously referred to by names such as "single use cameras", "lens with film", or "photosensitive material package units".

Another type of color negative element is a color print. Such an element is designed to receive an image optically printed from an image capture color negative element. A color print element may be provided on a reflective support for reflective viewing (e.g. a snap shot) or on a transparent support for projection viewing as in a motion picture. Elements destined for color reflection prints are provided on a reflective support, typically paper, employ silver chloride emulsions, and may be optically printed using the so-called negative-positive process where the element is exposed to light through a color negative film which has been processed as described above. The element is sold with instructions to process using a color negative optical printing process, for example the Kodak RA-4 process, as generally described in PCT WO 87/04534 or U.S. Pat. No. 4,975,357, to form a positive image. Color projection prints may be processed, for example, in accordance with the Kodak ECP-2 process as described in the H-24 Manual. Color print development times are typically 90 seconds or less and desirably 45 or even 30 seconds or less.

A reversal element is capable of forming a positive image without optical printing. To provide a positive (or reversal) image, the color development step is preceded by development with a non-chromogenic developing agent to develop exposed silver halide, but not form dye, and followed by uniformly fogging the element to render unexposed silver halide developable. Such reversal emulsions are typically sold with instructions to process using a color reversal process such as the Kodak E-6 process as described in The British Journal of Photography Annual of 1988, page 194. Alternatively, a direct positive emulsion can be employed to obtain a positive image.

The above elements are typically sold with instructions to process using the appropriate method such as the mentioned color negative (Kodak C-41), color print (Kodak RA-4), or reversal (Kodak E-6) process.

Preferred color developing agents are p-phenylenediamines such as:

4-amino-N,N-diethylaniline hydrochloride, 4-amino-3-methyl-N,N-diethylaniline hydrochloride, 4-amino-3-methyl-N-ethyl-N-(2-methanesulfonamidoethyl)aniline sesquisulfate hydrate, 4-amino-3-methyl-N-ethyl-N-(2-hydroxyethyl)aniline sulfate, 4-amino-3-(2-meth anesulfonamidoethyl)-N,N-diethyl aniline hydrochloride, and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

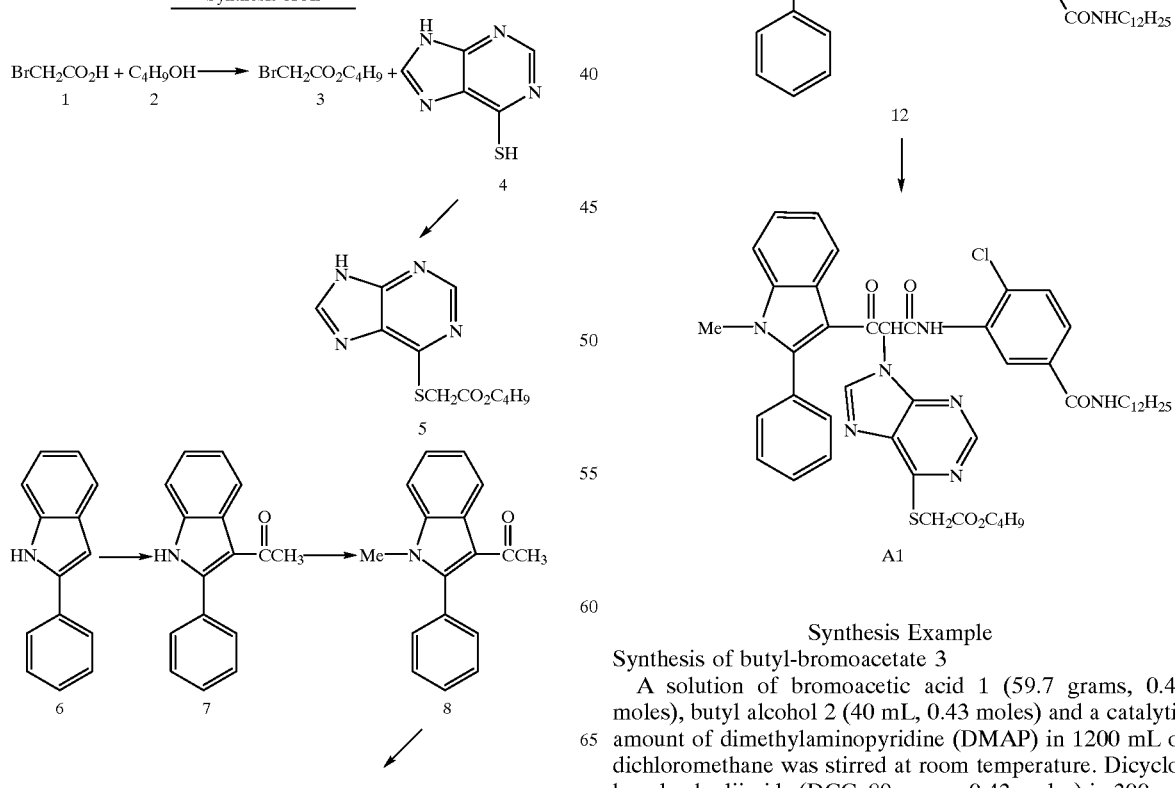

Synthesis Example

Synthesis of butyl-bromoacetate 3

A solution of bromoacetic acid 1 (59.7 grams, 0.43 moles), butyl alcohol 2 (40 mL, 0.43 moles) and a catalytic amount of dimethylaminopyridine (DMAP) in 1200 mL of dichloromethane was stirred at room temperature. Dicyclohexylcarbodiimide (DCC, 89 grams, 0.43 moles) in 300 mL of dichloromethane was then added dropwise. After addition was complete, the reaction was allowed to stir at room temperature for 30 minutes. The solid that precipitated was removed by filtration and discarded. The solvent was removed under vacuum. The structure was confirmed as 3 by NMR spectroscopy. The resulting oil was used without further purification in the preparation of 5.

Synthesis of 5

A solution of 6-mercaptopurine 4, (75 grams, 0.44 moles) and sodium methoxide (25 w % solution in methanol, 95 grams, 0.48 moles) in methanol (800 mL) was treated in one portion with hexyl-bromoacetate 3 as a solution in 200 mL of methanol. The solution was allowed to stir at ambient temperatures for 1.5 hours. The reaction was diluted with 800 mL of water. Within one hour, a solid formed. This was filtered and air dried to give 71 grams of 5 (61%). The structure was confirmed by NMR spectroscopy.

Synthesis of 7

Dimethylacetamide (700 mL) was placed in a 2 liter 3-neck round bottom flask equipped with a thermometer, mechanical stirrer and addition funnel. The mechanically stirred liquid was cooled to $-5°$ C. with an ice/acetone bath. Phosphorousoxychloride ($POCl_3$, 100 mL, 1.07 moles) was added dropwise over a sixty minute period. During this time the temperature rose to 5° C. After addition was complete, 2-phenyl indole 6 (193 grams, 1.0 mole) was added portionwise over a 10 minute period. The ice bath was removed and replaced with a heating mantle. The temperature was raised to ≈50° C. for one hour and then to ≈85° C. for two hours. Thin layer chromatography (TLC, ethyl acetate 20%, heptane 80%) on the solution showed no starting material and only faint impurities. The solution was poured into a 3 liter mixture of crushed ice and water with stirring. Within a few minutes the stirred suspension set up to a dark green solid. To this, 500 grams of 50% aqueous sodium hydroxide was added. The mixture exothermed from 10° C. to 50° C. The suspension broke up and became orange colored. The mechanically stirred suspension was heated to 95° C. for one hour, then cooled to 50° C., and 250 mL of concentrated HCl was added slowly. The mixture was mechanically stirred overnight. The solid which formed was filtered, and recrystallized from methanol to give a tan solid 7 (207 grams, 88% yield). The structure was confirmed by NMR spectroscopy.

Synthesis of 8

The indole 7 (150 grams, 0.64 moles) was placed in a 3 liter Morton flask, equipped with a mechanical stirrer and thermometer. The flask was charged with 1200 mL of toluene and the suspension was vigorously stirred. To this, dimethylsulfate (73 mL, 0.77 moles) was added, then 50% aqueous sodium hydroxide (100 mL, 1.9 moles) was added, followed by a catalytic amount of tetrabutylammonium bromide (5 grams). After fifteen minutes an exotherm was noticed. Within an hour the solid was in solution. TLC (ethyl acetate 20%, heptane 80%) showed no starting material 7, and one new spot. The solution was diluted with two liters of water and one liter of ethyl acetate. The aqueous layer was separated from the organic layer and discarded. The organic layer was dried with magnesium sulfate, filtered and concentrated to near dryness. To this, 3 liters of low- boiling ligroin was added. The slightly colored solid which formed was filtered and air dried to give 117 grams of 8 (75%). The structure was confirmed by NMR spectroscopy.

Synthesis of 9

A mechanically stirred solution of 8 (107 grams, 0.43 moles) in dimethylformamide (340 mL) and dimethylcarbonate (360 mL, 4.3 moles) was treated in portions with potassium tert-butoxide (144 grams, 1.3 moles). The solution was stirred at ambient temperatures for two hours. TLC (ethyl acetate 25%, heptane 75%) showed no starting material and one new spot. One liter of cold dilute HCl was added slowly to the reaction mixture. The solid that formed was filtered and air dried to give 113 grams of a yellow solid 9 (86% yield). The structure was confirmed by NMR spectroscopy.

Synthesis of 11

A stirred suspension of 9 (16.1 grams, 0.05 moles) and benzamide, 4-amino-3-chloro-N-dodecyl 10 (17.8 grams, 0.05 moles) in 200 mL of xylenes was heated to reflux into a Dean Stark trap for eight hours. During this time, 100 mL of xylenes was removed via the Dean Stark trap. After four hours, TLC (ethyl acetate 40%, heptane 60%) showed no starting material and one major new spot. The solution was cooled to room temperature, placed on a column of silica gel and chromatographed, eluting with heptane 100%, ethyl acetate 0% up to heptane 75%, ethyl acetate 25%. The solvent was removed under reduced pressure to give 11 as a red oil (29.5 grams, 91% yield). The structure was confirmed by NMR spectroscopy.

Synthesis of 12

A stirred suspension of 11 (29 grams, 0.05 moles) in 300 mL of toluene was heated to 80° C. until everything was in solution. Dibromodimethylhydantoin (8.1 grams, 0.028 moles) was added to the solution in one portion. The reaction mixture was stirred at 80° C. for one hour. TLC (ethyl acetate 40%, heptane 60%) showed no starting material and one major new spot. The reaction mixture was cooled to room temperature, placed on a column of silica gel and chromatographed, eluting with heptane 100%, ethyl acetate 0% up to heptane 70%, ethyl acetate 30%. The solvent was removed under reduced pressure to give a red oil. The oil was mechanically stirred in under isopropyl ether for 24 hours. During this time period the oil solidified. The solid was filtered and air dried to give 18.2 grams of 12 (56% yield) as a tan solid The structure was confirmed by NMR spectroscopy.

Synthesis of A1

A solution of 5 (3.8 grams, 0.014 moles) in 50 mL of dimethylacetamide (DMAc) was treated with potassium tert-butoxide (1.2 grams, 0.011 moles) in one portion. The solution was stirred at ambient temperature for ten minutes. To this, a solution of 12 (5.0 grams, 0.007 moles) in 100 mL of DMAc was added in one portion. The reaction mixture was stirred at ambient temperature for thirty minutes. TLC (ethyl acetate 40%, heptane 60%) showed no starting material and one major new spot. The reaction was partitioned between dilute HCl and ethyl acetate. The product was extracted into the organic layer, dried with magnesium sulfate, and concentrated to an oil. The oil was dissolved in toluene and chromatographed, eluting with heptane 90%, ethyl acetate 10% up to heptane 70%, ethyl acetate 30%. The solvent was removed under reduced pressure to give a yellow oil. The oil was stirred under isopropyl ether for 12 hours. During this time period a solid crystallized from the mixture. The solid was filtered and air dried to give 2.4 grams (38% yield) of A1. The structure was confirmed by NMR and mass spectroscopy. Combustion analysis, theory: C 65.6, H 6.4, N 11.2, Cl 4.0, S 3.7 found: C 65.4, H 6.4, N 11.2, Cl 4.3, S 4.0.

EXAMPLE 1

Illustration of Improved Inhibition Efficiency Provided by the DIR Couplers of this Invention To illustrate the superior inhibition efficiency and interlayer interimage provided by the DIR couplers of this invention, couplers A1 and A2 of this invention and comparative DIR coupler IR-1 were evaluated in the multilayer causer/receiver format shown in Table I. Structures of components that were not given previously are provided after Table II. Component laydowns in g/sq m are given in Table I in parentheses. The DIR couplers were all coated at a level of 0.129 mmole/sq m. DIR coupler IR-1 is suitable for comparison, since it is utilized advantageously in many commercial color negative films.

All DIR couplers were dispersed at a 1:1 weight ratio in dibutyl phthalate (S-2). The dispersions were prepared by adding an oil phase containing a 1:1:3 weight ratio of DIR coupler:S-2:ethyl acetate to an aqueous phase containing gelatin and the dispersing agent ALKANOL XC(Dupont) (mixed isomers of triisopropyl-2-naphthalene sulfonic acid, sodium salt) in a 10:1 weight ratio. The mixture was then passed through a colloid mill to disperse the oil phase in the aqueous phase as small particles. On coating, the ethyl acetate auxiliary solvent evaporates. Coupler Y-1 was dispersed with tritolyl phosphate (S-1, mixed isomers) at a 1:0.5 weight ratio.

Film samples were given a sensitometric white light (neutral) exposure and processed in a KODAK FLEXICOLOR C-41 process as in Table II. Blue (causer) and green (receiver) status M densities vs exposure were then measured for check film A without DIR coupler and for films with the comparative DIR coupler and DIR couplers of this invention. Blue and green gamma values were then obtained from slopes of the plots of density vs log exposure. It is desirable that DIR couplers efficiently reduce gamma or contrast in the layer or color record in which they are coated to provide benefits such as enhanced sharpness, reduced granularity and improved exposure latitude. For high interlayer interimage and high color correction it is desirable that a DIR coupler produce substantial gamma reduction in receiver layers without too much gamma reduction in its own (causer) layer. In this case blue gamma corresponds to causer gamma and green gamma to receiver gamma. Blue and green gammas from neutral exposures are given in Table III.

TABLE I

| OVERCOAT: | Gelatin (5.38) |
| | Bis(vinylsulfonyl)methane Hardener (0.281) |
| CAUSER: | Y-1 (0.861) & S-1 (0.430) |
| and | A) No DIR Coupler (Uninhibited Check) |
| or | B) IR-1 (0.098) & S-2 (0.098) Comparison |
| or | C) A1 (0.113) & S-2 (0.113) Invention |
| or | D) A2 (0.118) & S-2 (0.118) Invention |
| | Green-Sens. 0.46 μm Silver Iodobromide |
| | Emulsion (0.807 Ag) |
| | Gelatin (2.69) |
| INTERLAYER: | IS-1 (0.054) & S-1 (0.054) |
| | Gelatin (0.86) |
| RECEIVER: | M-1 (0.430), S-1 (0.344) & ST-1 (0.086) |
| | Red-Sens. 0.46 μm Silver Iodobromide |
| | Emulsion (0.807 Ag) |
| | Tetraazaindene (0.019) |
| | Gelatin (2.69) |
| Cellulose Acetate Support with Gel U-Coat and Antihalation Backing | |

TABLE II

C-41 Processing Solutions and Conditions

| Solution | Process Time | Agitation Gas |
| --- | --- | --- |
| C-41 Developer | 3'15" | Nitrogen |
| Stop Bath | 30" | Nitrogen |

TABLE II-continued

C-41 Processing Solutions and Conditions

| Solution | Process Time | Agitation Gas |
| --- | --- | --- |
| Wash | 2'00" | None |
| Bleach | 3'00" | Air |
| Wash | 3'00" | None |
| Fix | 4'00" | Nitrogen |
| Wash | 3'00" | None |
| Wetting Agent Bath | 30" | None |

Process temperature 38 C.

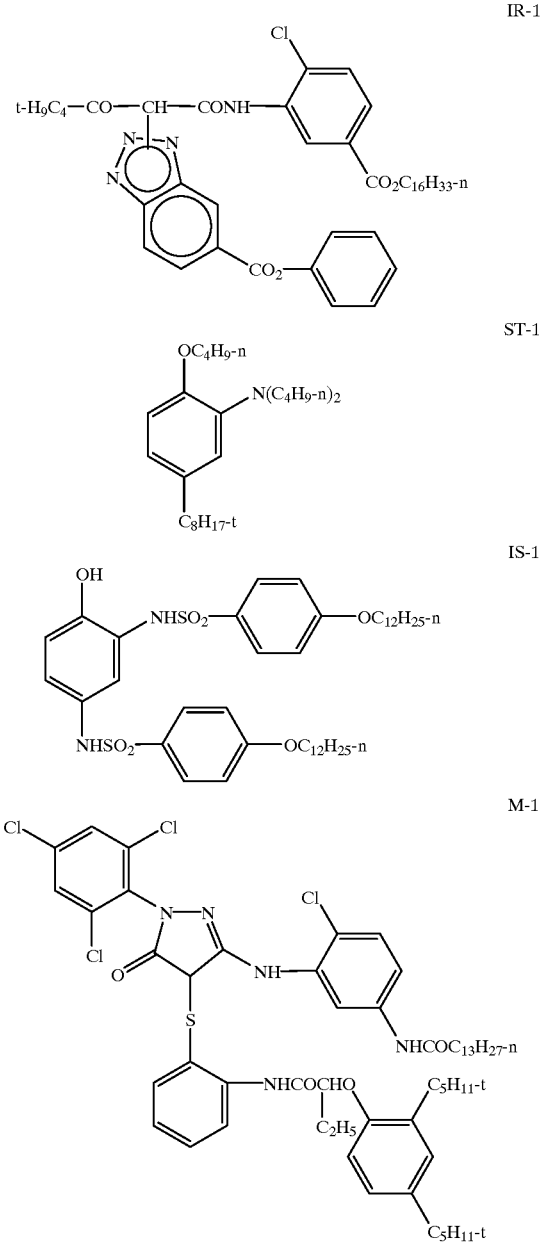

TABLE III

| Coating | DIR Coupler | Blue Gamma | Green Gamma |
|---|---|---|---|
| A | None (Check) | 1.72 | 1.48 |
| B | IR-1 (Comparison) | 1.21 | 1.00 |
| C | A1 (Invention) | 0.98 | 0.82 |
| D | A2 (Invention) | 0.97 | 0.85 |

From the data in Table III it is apparent couplers A1 and A2 of this invention provide a substantially greater reduction in blue gamma than comparative coupler IR-1 coated at the same molar laydown. Thus, the benefits of improved sharpness, reduced granularity and increased exposure latitude associated with a reduction in blue contrast are more efficiently provided by couplers A1 and A2 of this invention. In addition, couplers A1 and A2 of this invention, provide proportionally larger decreases in green gamma or receiver gamma than does comparative coupler IR-1. This means that couplers A1 and A2 of this invention will provide more efficient color correction via interlayer interimage than comparative DIR coupler IR-1. Often when a DIR coupler is more efficient in reducing gamma values in a causer layer, it is less effective in reducing receiver gamma values. Surprisingly, the DIR couplers of this invention show desirable efficiency increases with respect to BOTH causer and receiver gamma reductions.

The inhibitor released from couplers A1 and A2 of this invention is readily hydrolyzed in the C-4 1 developer solution, which prevents unwanted sensitometric effects associated with the accumulation of inhibitor in the developer upon extensive processing of film samples. DIR couplers A1 and A2 also have superior thermal stability. After storage for two weeks at 60 C/50% relative humidity, there was only 2% decomposition of coupler A1 in film C and 0% decomposition of coupler A2 in film D, above.

The dyes formed from couplers A1 and A2 of this invention also offer several advantages. They have extinction coefficients in film of approximately 25,000 cm sq/mmole, versus about 17,000 cm sq/mmole for the yellow dye formed from IR-1. This allows less silver and/or coupler to be coated to obtain the same blue density. The dyes formed from A1 and A2 are sharper cutting on the long wavelength side than the dye formed from IR-1, providing less unwanted green absorption and greater color purity. In addition, the dyes produced from couplers A1 and A2 are much more stable in a photographic element under long term storage or storage at high temperatures.

EXAMPLE 2

Multilayer Films Comparing Commercial Yellow DIR Coupler IR-1 and Yellow DIR coupler A1 of This Invention For this example, a multilayer color negative film containing comparative DIR coupler IR-1 was compared to a film containing DIR coupler A1, coated at a 80% of the molar laydown of IR-1. The multilayer film structure utilized in this example is shown schematically in Table IV. Structures of components not provided previously are given immediately following Table IV. Component laydowns are provided in units of g/sq m unless otherwise indicated. This composition may also be coated on a support, such as polyethylene naphthalate, containing a magnetic recording layer. These films were given neutral exposures and processed using KODAK FLEXICOLOR C-41 processing chemistry. Results are compared below.

TABLE IV

MULTILAYER FILM STRUCTURE

1 Overcoat & UV Layer:

Matte Beads
    UV Absorbers UV-1 (0.108), UV-2 (0.108) &
    S-1 (0.151)
    Silver Bromide Lippmann Emulsion (0.215 Ag)
    Gelatin (1.237)
    Bis(vinylsulfonyl)methane Hardener
    (1.75% of Total Gelatin)

2 Fast Yellow Layer:

Y-1 (0.236) Yellow Dye-Forming Coupler & S-1 (0.118)
  and E IR-1 (0.076) Comparative DIR Coupler & S-1 (0.038)
  or F A1 (0.070) DIR Coupler of Invention & S-2 (0.070)
    B-1 (0.0054) BARC & S-3 (0.0070)
Blue Sensitive Silver Iodobromide Emulsion (0.377 Ag),
    4.1 mole % Iodide T-Grain (2.9 × 0.12 μm)
Blue Sensitive Silver Iodobromide Emulsion (0.108 Ag)
    4.1 mole % Iodide T-Grain (1.9 × 0.14 μm)
    Gelatin (0.807)

3 Slow Yellow Layer:

Y-1 (1.076) & S-1 (0.538)
  and E IR-1 (0.076) (Comparative) & S-1 (0.038)
  or F A1 (0.070) (Invention) & S-2 (0.070)
    B-1 (0.022) & S-3 (0.0028)
    CC-1 (0.032) & S-2 (0.064)
    IR-4 (0.032) & S-2 (0.064)
Blue Sensitive Silver Iodobromide Emulsion (0.398 Ag),
    4.1 mole % Iodide T-Grain (1.9 × 0.14 μm)
Blue Sensitive Silver Iodobromide Emulsion (0.269 Ag),
    1.3 mole % Iodide T-Grain (0.54 × 0.08 μm)
Blue Sensitive Silver Iodobromide Emulsion (0.247 Ag)
    1.5 mole % Iodide T-Grain (0.77 × 0.14 μm)
    Gelatin (1.872)

4 Yellow Filter Layer:

R-1 (0.086) & S-2 (0.139) & ST-2 (0.012)
    YD-2 Filter Dye (0.054)
    Gelatin (0.646)

5 Fast Magenta Layer:

M-1 (0.075) Magenta Dye-Forming Coupler &
    S-1 (0.068) & ST-1 (0.0075), Addendum, R-2 (0.009)
    MM-1 (0.054) Masking Coupler & S-1 (0.108)
    IR-2 (.030) DIR Coupler & S-2 (0.060)
    B-1 (0.003) & S-3 (0.004)
Green Sensitive Silver Iodobromide Emulsion (0.484 Ag),
    4.0 mole % Iodide T-Grain (1.60 × 0.12 μm)
    Gelatin (1.014)

6 Mid Magenta Layer:

M-1 (0.124) & S-1 (0.111) & ST-1 (0.012)
    MM-1 (0.118) & S-1 (0.236), R-2 (0.015)
    IR-3 (0.043) DIR Coupler & S-2 (0.043)
Green Sensitive Silver Iodobromide Emulsion (0.247 Ag),
    4.0 mole % Iodide T-Grain (1.20 × 0.11 μm)
Green Sensitive Silver Iodobromide Emulsion (0.247 Ag)
    4.0 mole % Iodide T-Grain (1.00 × 0.12 μm)
    Gelatin (1.216)

7 Slow Magenta Layer:

M-1 (0.269) & S-1 (0.242) & ST-1 (0.027)
    MM-1 (0.086) & S-1 (0.172)
    IR-3 (0.011) & S-2 (0.011)
Green Sensitive Silver Iodobromide Emulsion (0.344 Ag),
    3.5 mole % Iodide T-Grain (0.90 × 0.12 μm)
Green Sensitive Silver Iodobromide Emulsion (0.129 Ag),
    1.5 mole % Iodide T-Grain (0.50 × 0.08 μm)
    Gelatin (1.076)

8 Interlayer:

R-1 (0.086) Interlayer Scavenger, S-2 (0.139)
    & ST-2 (0.012)
    Gelatin (0.538)

TABLE IV-continued

MULTILAYER FILM STRUCTURE

9 Fast Cyan Layer:

CC-1 (0.183) Cyan Dye-Forming Coupler & S-2 (0.210)
    CM-1 (0.022) Masking Coupler
    IR-4 (0.027) DIAR Coupler & S-2 (0.054)
Red Sensitive Silver Iodobromide Emulsion (0.592 Ag),
    4.1 mole % Iodide T-Grain (1.7 × 0.12 μm)
    Gelatin (0.915)

10 Mid Cyan Layer:

CC-1 (0.170) & S-2 (0.190)
    CM-1 (0.032)
    B-1 (0.008) & S-3 (0.010)
    IR-4 (0.019) & S-2 (0.038)
Red Sensitive Silver Iodobromide Emulsion (0.194 Ag),
    4.1 mole % Iodide T-Grain (1.2 × 0.11 μm)
Red Sensitive Silver Iodobromide Emulsion (0.236 Ag),
    4.1 mole % Iodide T-Grain (0.91 × 0.11 μm)
    Gelatin (1.076)

11 Slow Cyan Layer:

CC-1 (0.533) & S-2 (0.560)
    IR-4 (0.026) & S-2 (0.052)
    CM-1 (0.031)
    B-1 (0.056) & S-3 (0.073)

TABLE IV-continued

MULTILAYER FILM STRUCTURE

Red Sensitive Silver Iodobromide Emulsion (0.463 Ag),
    1.5 mole % Iodide T-Grain (0.54 × 0.06 μm)
Red Sensitive Silver Iodobromide Emulsion (0.301 Ag)
    4.1 mole % Iodide T-Grain (0.53 × 0.12 μm)
    Gelatin (1.679)

12 Antihalation Layer:

Gray Silver (0.135)
    UV-1 (0.075), UV-2 (0.030), S-1 (0.042), S-4 (0.015)
    YD-1 (0.034), MD-1 (0.018) & S-5 (0.018)
    CD-1 (0.025) & S-2 (0.125)
    R-1 (0.161), S-2 (0.261) & ST-2 (0.022)
    Gelatin (2.044)

Cellulose Triacetate Support

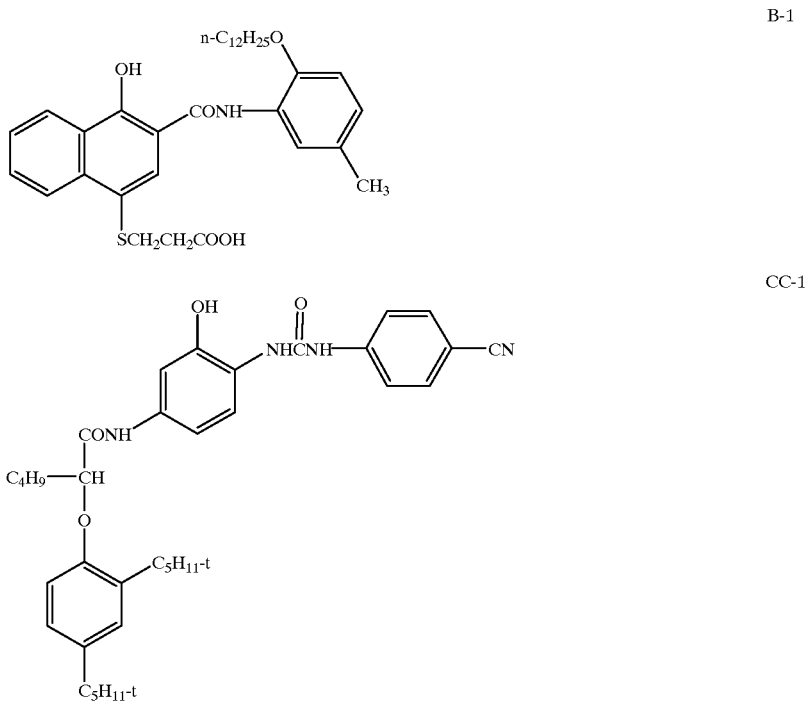

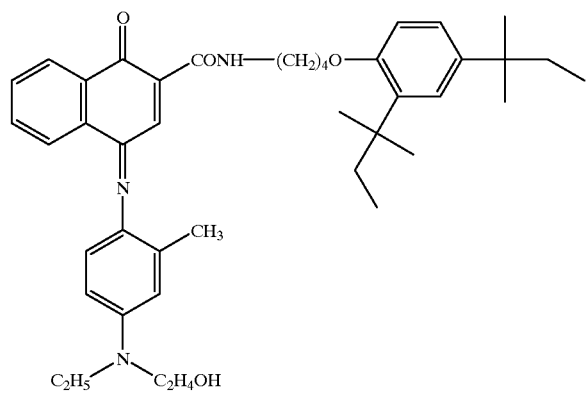
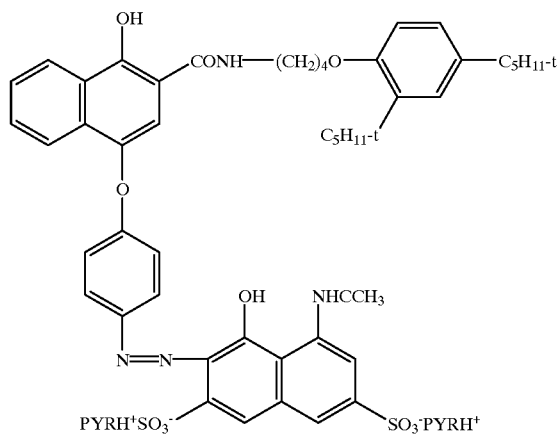
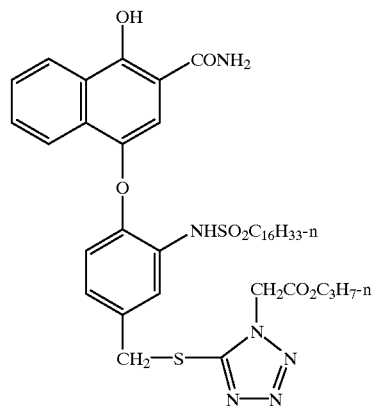
CD-1
CM-1
IR-3

IR-4
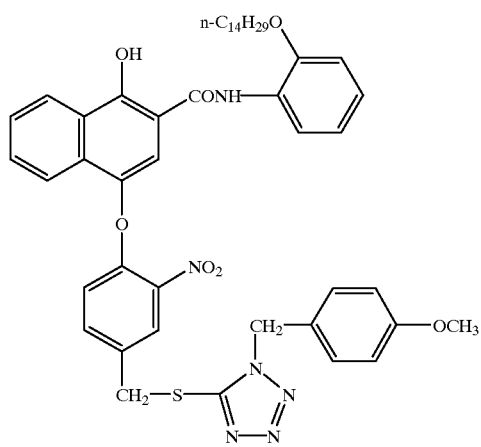
M-1
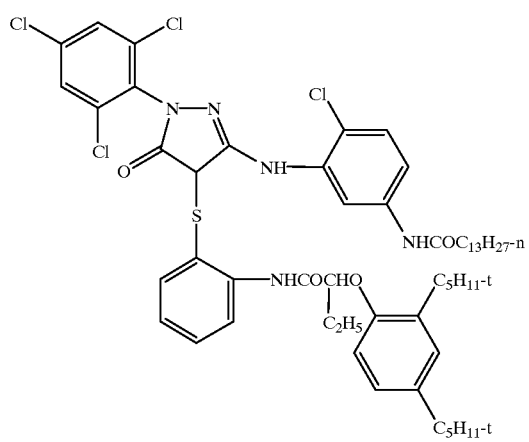
MD-1
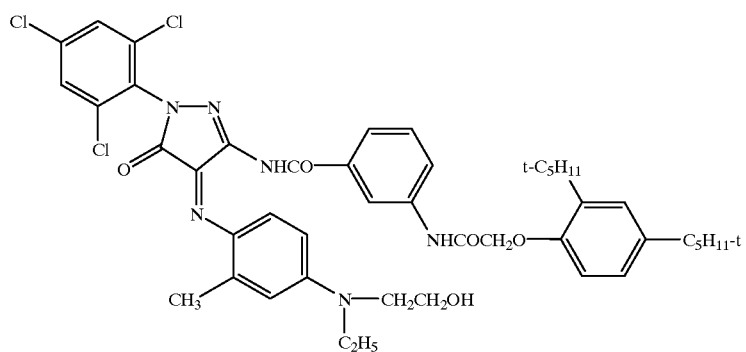

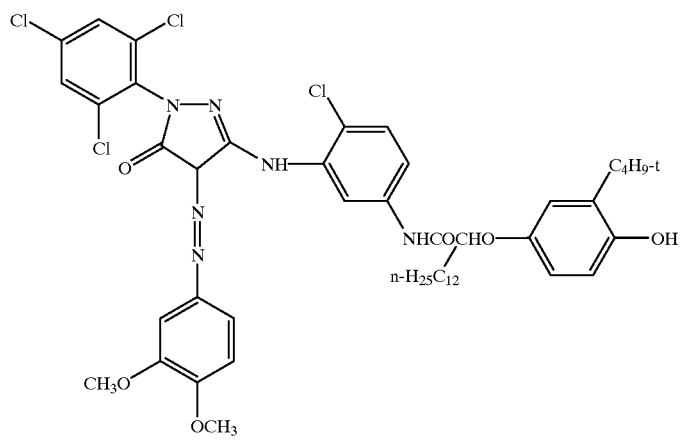
MM-1
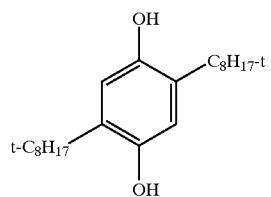
R-1
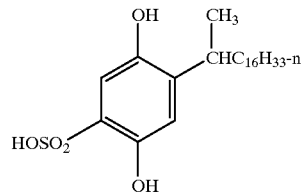
R-2
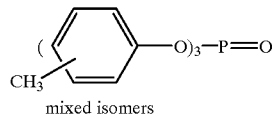
S-1
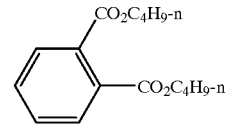
S-2
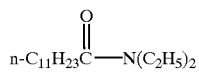
S-3
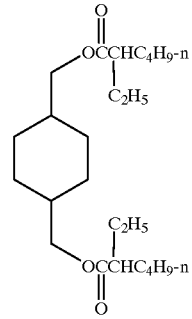
S-4

-continued

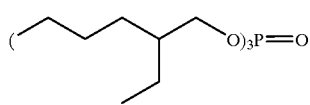

S-5

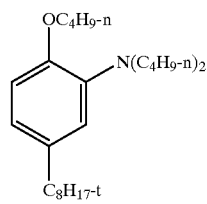

ST-1

ST-2

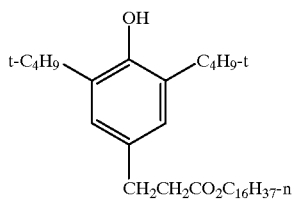

UV-1

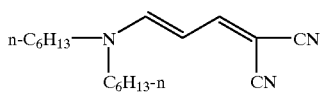

UV-2

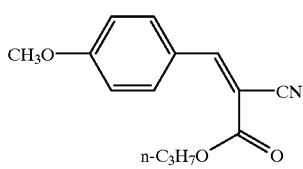

YD-1

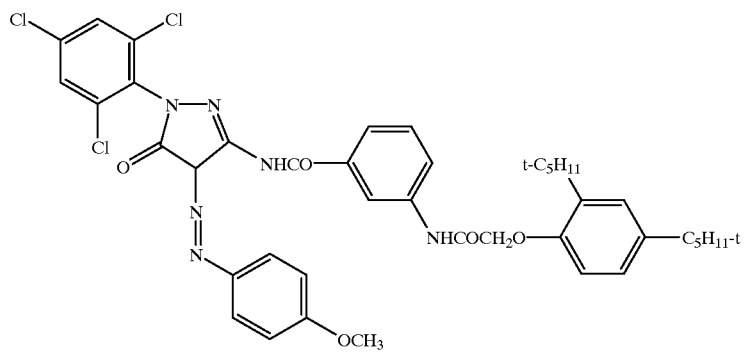

YD-2

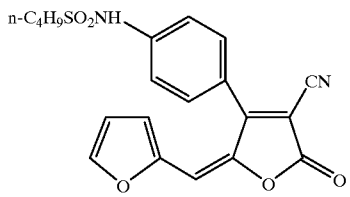

Exposed and processed films E and F above, containing couplers IR-1 and A1, respectively, yielded very similar green and red contrast. This implies that a similar degree in blue onto green and blue onto red interimage is provided by IR-1 and by A1 coated at only 80% of the laydown of IR-1. The blue contrast was higher for coating F containing coupler A1 (0.657 in the lower scale) than for coating E containing IR-1 (0.606 in the lower scale). This would allow desirable reductions in yellow imaging coupler and/or silver halide in the formulation of coating F, which may reduce cost and improve sharpness. Film F containing DIR coupler A1 of this invention also showed slightly improved blue speed relative to film E.

In addition, film F containing DIR A1 showed improved raw stock keeping. When exposed and processed after storage for 4 weeks at 49 C/50% relative humidity, film E containing IR-1 showed a significant loss in blue density and contrast, whereas film F containing DIR coupler A1 of this invention showed negligible loss in blue density or contrast.

The preceding examples are set forth to illustrate specific embodiments of this invention and are not intended to limit the scope of the compositions, materials or methods of the invention. Additional embodiments and advantages within the scope of the claimed invention will be apparent to one skilled in the art.

What is claimed is:

1. A photographic element, comprising a support bearing at least one silver halide emulsion and at least one 3-indoloylacetanilide yellow dye-forming DIR coupler of structure I, below:

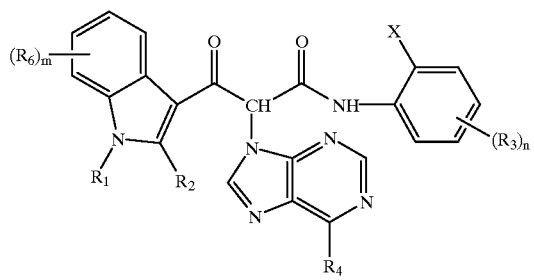

wherein:
- $R_1$ is an alkyl or phenyl group;
- $R_2$ is a phenyl, t-butyl, cyclohexyl or naphthyl group;
- X is a halogen atom or an alkoxy or alkyl group;
- each $R_3$ is in the para position or either meta position relative to the anilino nitrogen and is individually selected from the group consisting of halogen atoms, and alkyl, phenyl, alkoxy, phenoxy, carbamoyl, sulfamoyl, carbonamido, sulfonamido, alkylsulfonyl, arylsulfonyl, alkoxycarbonyl, aryloxycarbonyl, acyloxy, sulfoxyl, sulfonyloxy, alkylthio, acyl and cyano groups;
- n is 1, 2 or 3;
- $R_4$ contains at least two carbon atoms and is an alkylthio group or a carbonamido group represented by —NHCOR$_5$, wherein $R_5$ contains at least four carbon atoms and is an alkyl, phenyl, alkoxy or phenoxy group;
- each $R_6$ is individually a halogen atom, an alkyl group or an alkoxy group and m is 0–4;
- provided that substituents may join to form a ring.

2. A photographic element according to claim 1, wherein the 3-indoloylacetanilide DIR coupler is coated in the same layer with at least one blue sensitive silver halide emulsion.

3. A photographic element according to claim 2, wherein the blue sensitive silver halide emulsion is a tabular grain emulsion.

4. A photographic element according to claim 1, wherein $R_2$ is a phenyl group.

5. A photographic element according to claim 1, wherein $R_1$ is an alkyl group.

6. A photographic element according to claim 1, wherein X is a halogen atom.

7. A photographic element according to claim 1, wherein n is 1 and $R_3$ is a carbamoyl group or a sulfamoyl group in either the 4- or 5-position relative to the anilino nitrogen, with X being in the 2-position relative to the anilino nitrogen.

8. A photographic element according to claim 1, wherein m is 0.

9. A photographic element according to claim 1, wherein $R_4$ is an alkylthio group of the form —SCH$_2$CO$_2$R$_7$, and wherein $R_7$ is an alkyl group with at least two carbon atoms or a phenyl group.

10. A photographic element according to claim 9, wherein $R_7$ is an alkyl group with three to eight carbon atoms.

11. A photographic element according to claim 1, wherein $R_4$ is a carbonamido group and $R_5$ contains five to eleven carbon atoms.

12. A photographic element according to claim 1, wherein DIR coupler I is coated at a level between 0.005 and 0.600 g/sq m.

13. A photographic element according to claim 1, wherein coupler I is selected from the group consisting of:

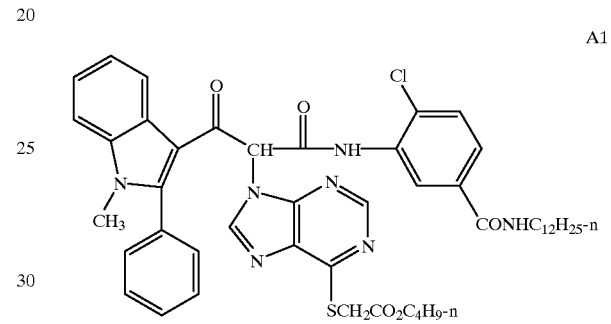

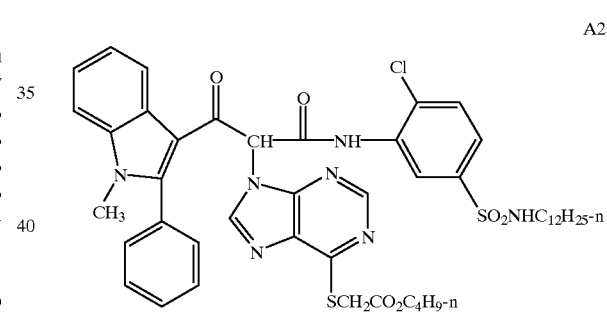

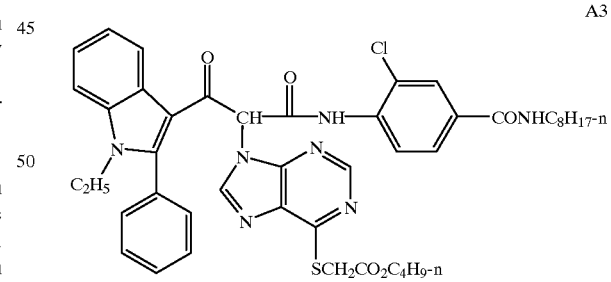

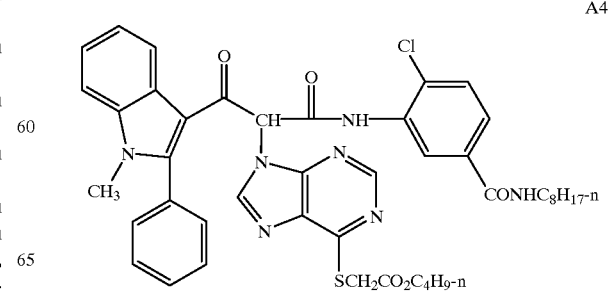

-continued

A5

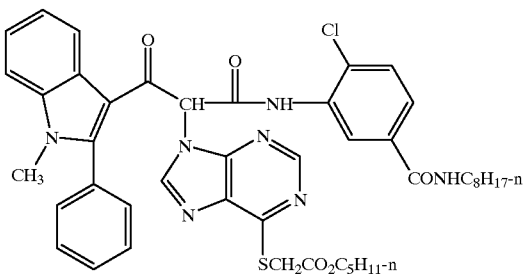
A6

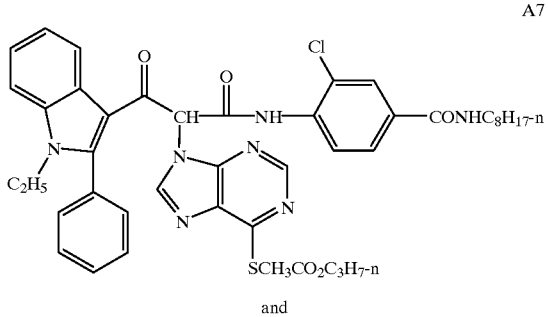
A7 and

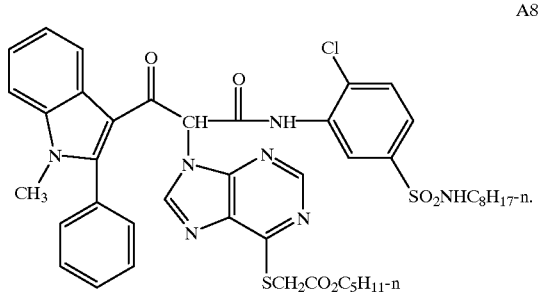
A8

14. A photographic element according to claim 1, wherein an imaging coupler of claim 1 is coated in the same layer as a yellow dye-forming imaging coupler of structure Y-1 or Y-2:

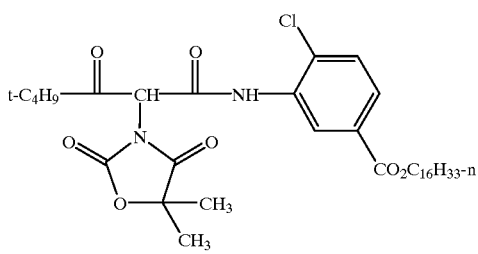
Y-1

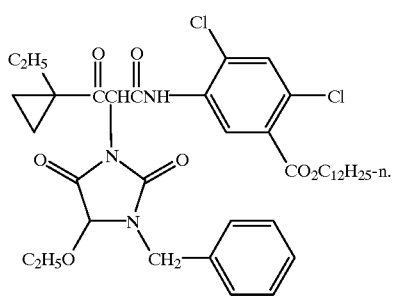
Y-2

15. A photographic element according to claim 1, wherein the support comprises a magnetic recording layer.

16. A multicolor photographic element comprising a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, said yellow dye-forming layer having Formula I:

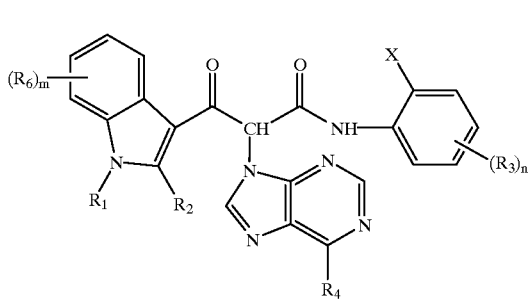
I wherein:
$R_1$ is an alkyl or phenyl group;
$R_2$ is a phenyl, t-butyl, cyclohexyl or naphthyl group;
X is a halogen atom or an alkoxy or alkyl group;
each $R_3$ is in the para position or either meta position relative to the anilino nitrogen and is individually selected from the group consisting of halogen atoms, and alkyl, phenyl, alkoxy, phenoxy, carbamoyl, sulfamoyl, carbonamido, sulfonamido, alkylsulfonyl, arylsulfonyl, alkoxycarbonyl, aryloxycarbonyl, acyloxy, sulfoxyl, sulfonyloxy, alkylthio, acyl and cyano groups;
n is 1, 2 or 3;
$R_4$ contains at least two carbon atoms and is an alkylthio group or a carbonamido group represented by —NHCOR$_5$, wherein $R_5$ contains at least four carbon atoms and is an alkyl, phenyl, alkoxy or phenoxy group;
each $R_6$ is individually a halogen atom, an alkyl group or an alkoxy group and m is 0–4;
provided that substituents may join to form a ring.

17. A method for forming an image comprising processing a photographic element according to claim 1 in a color developer solution.

* * * * *